US011679124B2

(12) United States Patent
Fändriks et al.

(10) Patent No.: US 11,679,124 B2
(45) Date of Patent: Jun. 20, 2023

(54) COMPOSITION FOR USE IN THE TREATMENT OF CONDITIONS CAUSED BY CALCIUM DEFICIENCY

(71) Applicant: Epicyt Pharma AB, Gothenburg (SE)

(72) Inventors: Lars Fändriks, Askim (SE); Ville Wallenius, Mölndal (SE)

(73) Assignee: Epicyt Pharma AB, Gothenburg (SE)

( * ) Notice: Subject to any disclaimer, the term of this patent is extended or adjusted under 35 U.S.C. 154(b) by 0 days.

(21) Appl. No.: 16/982,529

(22) PCT Filed: Mar. 19, 2019

(86) PCT No.: PCT/SE2019/050246
§ 371 (c)(1),
(2) Date: Sep. 18, 2020

(87) PCT Pub. No.: WO2019/182501
PCT Pub. Date: Sep. 26, 2019

(65) Prior Publication Data
US 2021/0000864 A1 Jan. 7, 2021

(30) Foreign Application Priority Data

Mar. 19, 2018 (SE) .................... 1850304-5

(51) Int. Cl.
| | |
|---|---|
| *A61K 33/06* | (2006.01) |
| *A23L 33/16* | (2016.01) |
| *A23L 33/155* | (2016.01) |
| *A61K 31/201* | (2006.01) |
| *A61K 31/592* | (2006.01) |
| *A61K 9/00* | (2006.01) |

(52) U.S. Cl.
CPC ............ *A61K 33/06* (2013.01); *A23L 33/155* (2016.08); *A23L 33/16* (2016.08); *A61K 31/201* (2013.01); *A61K 31/592* (2013.01); *A61K 9/0019* (2013.01); *A61K 9/0053* (2013.01)

(58) Field of Classification Search
CPC ............................ A61K 9/0019; A61K 9/0053
See application file for complete search history.

(56) References Cited

U.S. PATENT DOCUMENTS

| | | |
|---|---|---|
| 5,376,646 A | 12/1994 | Pittrof et al. |
| 2006/0052305 A1 | 3/2006 | Quay |
| 2007/0292493 A1 | 12/2007 | Brierre |
| 2010/0204191 A1 | 8/2010 | Makoto |
| 2011/0311621 A1* | 12/2011 | Salama ............... A61K 9/48 424/463 |
| 2014/0030352 A1* | 1/2014 | Khopade ............. A61K 9/10 424/501 |

FOREIGN PATENT DOCUMENTS

| | | |
|---|---|---|
| EP | 0252004 A1 | 6/1987 |
| EP | 1270007 B1 | 5/2004 |
| GB | 1601613 | 11/1981 |
| JP | 53107408 | 9/1978 |
| RU | 2 552 324 C2 | 6/2015 |

OTHER PUBLICATIONS

Sebastien Lucas, Short-chain fatty acids regulate systemic bone mass and protect from pathological bone loss, Nature Communications, 9:55, 2008 (Year: 2008).*
D. D'A. Webling, Bile Salts and Calcium Absorption, Biochem. J. (1966) 100 (Year: 1966).*
Mayo Clinic, Osteoporosis, Mayo Clinic Staff, publication date: Jun. 21, 2021 (Year: 2021).*
Laurene Boateng et al, Coconut oil and palm oil's role in nutrition, health and national development: A review, Ghana Med J 2016; 50(3): 189-196 (Year: 2016).*
Webling, D. D'A., et al. "The Effect of Bile, Bile Acids and Detergents on Calcium Absorption in the Chick", Biochem. J., 1965, vol. 97, pp. 408-421.
Marchionatti, A. et al. "Molecular Mechanisms Triggered by Bile Aids on Intestinal Ca2+ Absorption", Curr. Med. Chem., 2018, vol. 25, Issue 18, pp. 2122-2132, and 2124.
Hanley, R. et al., "Association between bile acid turnover and osteoporosis in postmenopausal women" Nucl. Med. Commun., 2013, vol. 34, No. 6, pp. 597-600.
Rodriguez, V. et al., "Ursodeoxycholic and deoxycholic acids: A good and a bad bile acid for intestinal calcium absorption", Arch. Biochem. Biophys., 2013, vol. 540, pp. 19-25.
Lucas, S. et al., "Short-chain fatty acids regulate systemic bone mass and protect from pathological bone loss", Nat. Commun., 2018, vol. 9, Issue 55, pp. 1-10.
Campbell, Y., et al., "Regulation of antimicrobial peptide gene expression by nutrients and by-products of microbial metabolism", Eur. J. Nutr., 2012, vol. 51, pp. 899-907.
Marchetti, G. M. et al. "Deoxycholic acid and SFCA-induced apoptosis in the human tumor cell-line HT-29 and possible mechanisms", Cancer Lett., 1997, vol. 114, pp. 97-99.
International Search Report dated May 27, 2019, issued in PCT/SE2019/050246.
Swedish Search Report dated Oct. 1, 2018, issued in Swedish Appln. No. 1850304-5.
Trinidad et al., Effect of Acetate and Propionate on Calcium Absorption from the Rectum and Distal Colon of Humans, Am. J. Clin, Nutr., vol. 63, pp. 574-578, 1996.

\* cited by examiner

*Primary Examiner* — Mark V Stevens
*Assistant Examiner* — Alparslan Asan
(74) *Attorney, Agent, or Firm* — Covington & Burling LLP

(57) ABSTRACT

The present invention is related to a composition comprising at least one bile acid; at least one fatty acid or salt thereof, calcium, and vitamin D, for use as a medicament, and especially in inducing expression of vitamin D-receptor co-activator Hsp90β for increasing vitamin D-induced calcium uptake in a mammal. The invention is also related to a dietary or nutritional supplement comprising a composition as described above and comprising additionally conventional components for dietary or nutritional supplements.

16 Claims, 4 Drawing Sheets

COMPOSITION FOR USE IN THE TREATMENT OF CONDITIONS CAUSED BY CALCIUM DEFICIENCY

FIELD OF THE INVENTION

The present invention is related to a composition comprising at least one bile acid or a salt thereof, at least one fatty acid or salt thereof. The composition may also comprise calcium, and vitamin D, and is for use as a medicament, especially for the treatment and/or prevention of disorders related to intestinal calcium uptake deficiency.

BACKGROUND OF THE INVENTION

The global obesity epidemic was calculated to affect more than 1.5 billion individuals in 2003 with an ever-increasing incidence globally. The rise in the prevalence of obesity is associated with increases in the prevalence of obesity comorbidities (e.g. type 2 diabetes, hyperlipidemia, hypertension, ischemic heart disease, stroke, asthma, back and lower extremity joint degenerative problems, several forms of cancer, depression etc.). Obesity is estimated to kill about 320 000 people a year in Western Europe. Thus, the loss of life expectancy due to obesity is profound. In comparison with a normal-weight individual, a 25-year-old morbidly obese man, will approximately have a mean loss of 12 years of life.

Bariatric surgery has in the last decades emerged as the only long-term effective treatment for morbid obesity. In systematic reviews, effective weight loss is achieved in morbidly obese patients after undergoing bariatric surgery. A substantial majority of patients with diabetes, hyperlipidemia, hypertension, and obstructive sleep apnea experience marked improvement, and sometimes complete resolution, after surgery. The most common form of bariatric surgery in Sweden is laparoscopic Roux-en-Y gastric bypass surgery (RYGB). A new emerging bariatric surgery method is sleeve gastrectomy (SG).

Usually postoperative recovery after laparoscopic bariatric surgery is quick. Rapid weight loss usually occurs during the first 6 to 12 months, leveling off at about two years after surgery. Life after gastric bypass means a changed pattern of food consumption, by smaller and more frequent meals. Because of the re-routing of the gastrointestinal tract, with foregut exclusion of food passage through the stomach and duodenum, and rapid hindgut delivery of undigested food to the jejunum i.e. alimentary limb, micronutrient uptake is attenuated. The bypassed stomach secretes less hydrochloric acid and intrinsic factor (IF), negatively affecting e.g. iron and vitamin B12 uptake. Therefore, lifelong vitamin B12, as well as multivitamin and trace mineral supplementation are recommended to all patients after RYGB. Iron supplementation is recommended to women before menopause, as well as to other patients with iron deficiency.

Active vitamin D-induced calcium uptake normally occurs in the proximal small intestine, i.e. duodenum and first half of the jejunum. Therefore, lifelong vitamin D and calcium supplementations are recommended to RYGB patients. Because of the re-routing of the small intestine after RYGB, the duodenum is bypassed from passage of nutrients. It has recently been shown that a co-activator of the vitamin D receptor, heat-shock protein (Hsp) 90β, as well as the most important vitamin D-induced calcium transport protein, TRPV6, are down-regulated in the alimentary limb mucosa after RYGB (Elias et al.). In line with this, it was also shown that RYGB, unlike vertical banded gastroplasty (VBG) patients, also had a procedure-dependent decrease of bone-mineral density (BMD). Thus, calcium- and vitamin D supplementation would seem to be of importance after RYGB to avoid risk of further decline of BMD and future osteoporosis fractures in these patients.

The recently introduced SG (sleeve gastrectomy) operation is effective for both weight loss and metabolic improvements, but the resection of the stomach is followed by a dramatic reduction of total gastric acid output and a shortened time for the transit of luminal contents to the distal small intestine. Functionally this condition partly mimics the effect of gastric bypass and thus lowers the ability for the mucosa to react on vitamin D and, in turn, reduces calcium absorption. Indeed, the SG procedure has been associated to signs of changed bone mineral turnover suggesting a risk for bone demineralization in the long run (Crawford et al.).

Following SG, as after RYBP, the patients are prescribed supplementation of vitamin D and calcium. However, it is not proven whether such supplementation can prevent a loss of BMD. There are actually data indicating that this may not be the case. For instance, a large fraction of RYGB patients that did receive calcium and vitamin D supplementation developed secondary hyperparathyroidism (SHPT), with increased PTH and decreased calcium levels, indicating that calcium absorption in the intestine may still be deficient despite supplementation (Hewit S et al.). It has also been found that patients on supplementation had a prominent increase of C-terminal telopeptide (CTX) levels 18 months after surgery, indicating increased bone turnover. There are also recent data showing that intestinal calcium absorption (fractional calcium absorption) is severely compromised and decreased by approximately 80% after RYGB, even when vitamin D levels were optimized (Schafer A L et al.). Therefore, calcium and vitamin D supplementation by the current regimens are not operational.

In addition, there is also another group of patients with a general decrease of bone-mineral density (BMD) and/or having a general decrease in calcium uptake and/or having a pathological bone condition, for instance osteoporosis caused by calcium deficiency, which could benefit from an increase in vitamin D-induced calcium uptake. Apart from vitamin D and calcium supplementation, a manifest bone mineralization disease is currently treated predominantly with systemic hormonal PTH supplementation or with pharmacological bone resorption inhibitors (like bisphonphonates, estrogen analogues, antibodies targeting resorption mechanisms etc.). Treatment regimens aiming at restoring intestinal calcium absorption capacity are few or often found nonfunctional.

U.S. Pat. No. 8,563,053 that discloses a composition comprising a nanoformulation of active ingredients comprising *Lepidium Sativum*, calcium, vitamin D and an antioxidant for treating a bone condition. Another example is WO2013/049595 that discloses methods and compositions for treatment of metabolic disorders by modulating bile acid levels.

In view of the above there is a need within the technical field to find solutions to above-mentioned problems, especially the decrease in vitamin D-induced calcium uptake and the decrease of bone-mineral density (BMD) in patients having gone through gastric surgery, e. g. in RYGB and SG patients.

SUMMARY OF THE INVENTION

The object of the present invention is to solve the above problem and to provide a composition comprising at least one bile acid or salt thereof, and at least one fatty acid or a salt thereof. The composition can also contain calcium, and vitamin D. The composition is intended for use as a medicament.

It has surprisingly been shown in connection with the present invention that a composition comprising at least one bile acid or a salt thereof, at least one fatty acid, or a salt thereof, synergistically induces expression of vitamin D-receptor co-activator Hsp90β and is followed by an increased calcium absorption in comparison with the two individual components, bile acid and fatty acid, respectively, alone. Therefore, a composition comprising all four components, thus, at least one bile acid or a salt thereof, at least one fatty acid, or a salt thereof, calcium, and vitamin D is provided.

It has previously been described that bone loss might be attributed to impaired calcium absorption caused by decreased activation of vitamin D-dependent calcium absorption mechanisms mediated by heat-shock protein 9013 (Elias et al.). Thus, the findings of the present invention would be of benefit to patients that have undergone bariatric surgery and generally to any patient suffering from conditions that may be helped by increased calcium absorption.

In an aspect of the invention, the treatment and/or prevention of calcium absorption deficiency.

Calcium absorption deficiency may occur, for example after a Roux-en-Y gastric bypass (RYGB). To compensate for this, and keep calcium levels in plasma up at normal levels, one compensatory mechanism that is commonly seen after RYGB is increased parathyroid hormone (PTH) production (Hewitt et al.). Operation of the thyroid gland is another surgical procedure that may cause deficiency of calcium absorption by negatively affecting the function of the parathyroid glands and their production of parathyroid hormone (PTH). There are reports in the literature that the combination of these two procedures, RYGB and thyroid surgery, may lead to severely decreased plasma calcium levels, and symptoms of hypocalcemia. The mechanism for this seems to be the inability to compensate for the decreased intestinal calcium absorption by increased PTH production. In some cases of combined RYGB and thyroid surgery, it has proven to be exceedingly difficult to treat the hypocalcemia (Goldenberg et al.). By administering the composition as herein defined the levels of calcium may be increased. This is of particular interest in patients where decreased calcium absorption causes decreased calcium levels in plasma, or decreased bone mineralization.

In another aspect of the invention, in the treatment and/or prevention of osteoporosis caused by calcium deficiency, malabsorption conditions caused by calcium deficiency or bone disorders caused by calcium deficiency in a mammal. Further, the composition may be used for treatment and/or prevention of osteoporosis by preventing bone mineral density (BMD) loss caused by calcium deficiency in a mammal. The composition may also be used for treatment of osteoporosis by preventing bone mineral density (BMD) loss in Roux-en-Y gastric bypass (RYGB) patients or sleeve gastrectomy (SG) patients.

Another aspect of the invention is the composition as defined herein wherein said at least one bile acid is chosen from primary bile acids and secondary bile acids and salts thereof. The bile acid is selected with the proviso that the bile acid is not taurocholic acid, or derivative thereof.

Another aspect of the invention is the composition wherein said at least one fatty acid is saturated or unsaturated, an example is wherein said at least one fatty acid is a short chain fatty acid (SCFA), a medium chain fatty acid (MCFA), a long chain fatty acid (LCFA) or a very long chain fatty acid (VLCFA). Particularly, the short fatty acid is butyric acid, or the medium chain fatty acid is oleic acid.

In an aspect of the invention, the composition for use comprising vitamin D, wherein the vitamin D consists mainly of vitamin D3. Another aspect of the invention is a composition wherein said calcium is present as calcium carbonate, calcium citrate, or calcium phosphate, or mixture thereof.

In an aspect of the invention, the amount of calcium and vitamin D in the composition is present as the recommended daily intake (RDI) or less. The composition may further comprise at least one of a vehicle, excipient, lubricant, flavour, sweetener, disintegrant, binder and disintegrant.

The composition as herein defined is formulated for oral delivery, parenteral delivery, intravenous infusion or injection. The composition may be in a liquid form, or solid form; the composition may be formulated as a chewing tablet, effervescent tablet, powder, pill, tablet or capsule.

In an aspect of the invention the composition is a nutritional or dietary supplement.

In an aspect of the invention the composition for use comprises a fatty acid being butyric acid or a salt thereof, said bile acid is glycocholic acid or a salt thereof, and vitamin D is vitamin D3.

BRIEF DESCRIPTION OF DRAWINGS

The invention will be more fully understood from the following detailed description taken in combination with the accompanying drawing, in which.

DETAILED DESCRIPTION OF THE INVENTION

Figure 1:
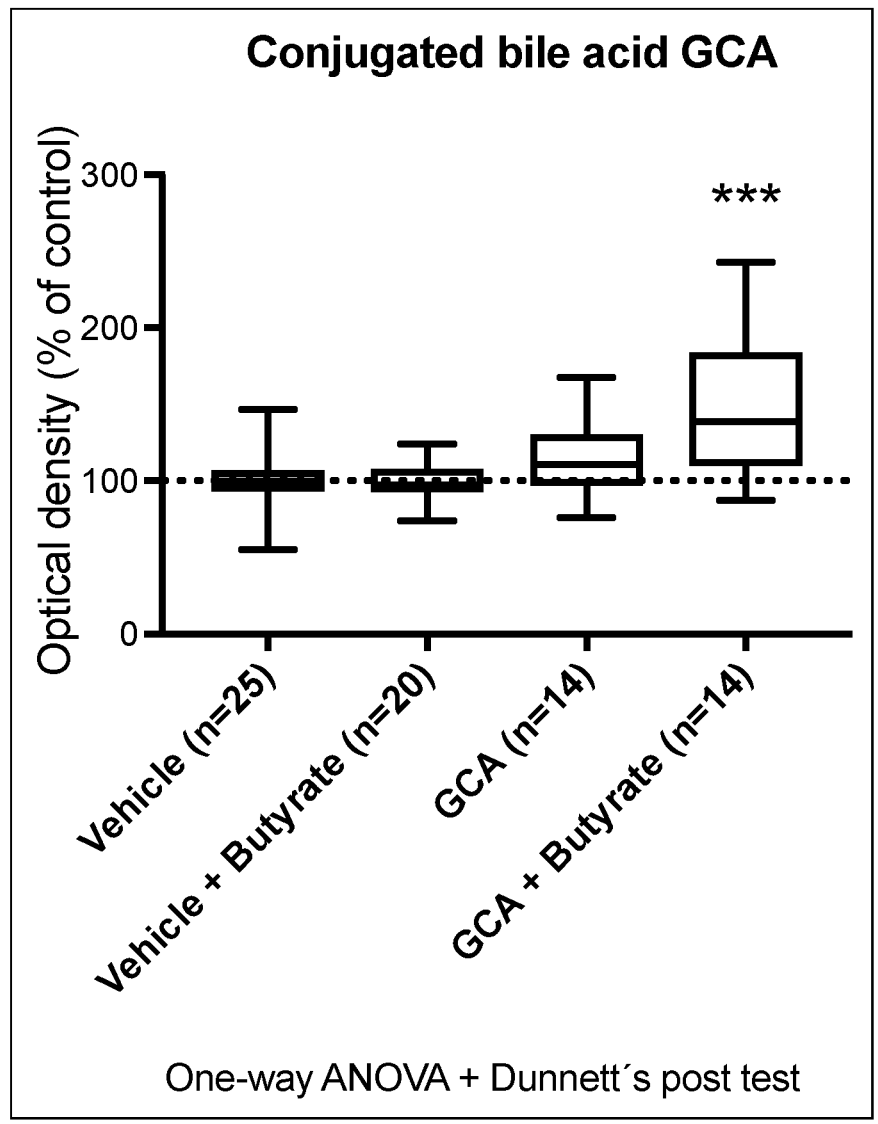
FIG. 1 discloses that the expression of heat-shock protein (Hsp) 90β, a co-activator of the vitamin-D receptor, is synergistically induced in Caco-2 cell culture by the addition of the bile acid GCA and the fatty acid butyrate together for 48 h, but not by either GCA or butyrate alone. GCA was added at a concentration of $1 \times 10^{-4}$ M and butyrate at a concentration of $5 \times 10^{-4}$ M. *** $P<0.001$; GCA+butyrate vs. control, unpaired t-test.

Certain exemplary embodiments will now be described to provide an overall understanding of the principles and function of the invention. Those skilled in the art will understand that the exemplary embodiments described are non-limiting and that the scope of the present invention is defined by the claims.

As indicated above, the present invention is related to a composition comprising a) at least one bile acid or salt thereof, b) at least one fatty acid or a salt thereof,
c) calcium, and
d) vitamin D.

The composition is intended for use as a medicament.

It has surprisingly been found observed according to the present invention that a composition comprising at least one bile acid or a salt thereof, at least one fatty acid, or a salt thereof, vitamin D, and calcium, synergistically induces expression of vitamin D-receptor co-activator Hsp90β.

By inducing expression of vitamin D-receptor co-activator, the vitamin D induced calcium transport can be substantially increased, i.e. normalized in patients suffering from calcium deficiency such as in RYGB patients and SG patients.

Hsp90β has a well-known stimulatory action on protein TRPV6 that is a protein involved in the transcellular active transport of calcium. However, active calcium transport is not to be sensitive to the compositions of interest. Instead, according to the present invention Hsp90β activates a vitamin D dependent increase in passive (paracellular) calcium passage. This is an important feature of the present invention: apart from vitamin D, also calcium as such must be included into the composition to obtain the transepithelial concentration gradient needed for paracellular transport.

In view of the above described induction of vitamin D-receptor co-activator Hsp90β, the compositions of the invention may be used in the treatment of any patient suffering from conditions that may be helped by increased calcium absorption. In such pathological conditions, e.g. osteoporosis, which may be caused by calcium deficiency due to malabsorption there is a need of preventing bone mineral density (BMD) loss. In mammals there are individuals being susceptible to such conditions. For instance, the compositions of the invention would be suitable in the treatment of patients such as elderly people suffering from osteoporosis caused by calcium deficiency.

The compositions of the invention are in one embodiment suitable for treatment and/or prevention of osteoporosis by preventing bone mineral density (BMD) loss in Roux-en-Y gastric bypass (RYGB) patients or sleeve gastrectomy (SG) patients.

The compositions according to the invention comprise at least one "bile acid", or a salt thereof, at least one "fatty acid" or a salt thereof, as well as calcium and vitamin D.

The phrase "bile acid" as used herein includes both those that are naturally occurring in living organisms as well as those that are synthetic bile acids. The naturally occurring bile acids may be both Primary bile acids, which are synthesized in the liver, and Secondary bile acids, which are the results of bacterial actions in the intestine. The naturally occurring bile acids may also be Conjugated bile acids, which means that the bile acid is conjugated on the carboxylic group with either a glycine or a taurine moiety, and which may be the case for both the primary and the secondary bile acids.

To the primary bile acids belong cholic acid (CA) and chenodeoxycholic acid (CDCA), and there corresponding conjugated forms are glycocholic acid (GCA) and taurocholic acid (TCA) as well as glycochenocholic acid (GCDCA) and taurochenodeoxycholic acid (TCDCA), respectively. Especially, the primary bile acids of interest for the present invention are cholic acid (CA) and chenodeoxycholic acid (CDCA), and their corresponding conjugated forms glycocholic acid (GCA) and glycochenocholic acid (GCDCA), respectively.

To the secondary bile acids belong deoxycholic acid (DCA), lithocholic acid (LCA), ursodeoxycholic acid (UDCA) and hyodeoxycholic acid (HDCA), and there corresponding conjugated forms are glycodeoxycholic acid (GDCA), taurodeoxycholic acid (TDCA), glycolithocholic acid (GLCA), turolithocholic acid (TLCA), glycoursodeoxycholic acid (GUDCA), tauroursodeoxycholic acid (TUDCA), glycohyodeoxycholic acid (GHDCA) and taurohyodeoxycholic acid (THDCA), respectively. Especially, the deoxycholic acid (DCA), lithocholic acid (LCA), ursodeoxycholic acid (UDCA) and hyodeoxycholic acid (HDCA), and their corresponding conjugated forms are glycodeoxycholic acid (GDCA), glycolithocholic acid (GLCA), glycoursodeoxycholic acid (GUDCA), and, glycohyodeoxycholic acid (GHDCA), respectively, are of interest for the present invention.

The conjugated bile acids are more acidic than the non-conjugated bile acids, and are therefore frequently called "bile salts". The different bile acids are the major constituents of the "bile" in the various organisms, but the abundance of the different particular bile acids, e.g. in different animals, can vary within large ranges. A synthetic bile acid is e.g. obeticholic acid (OCA) (6alpha-ethyl-chenodeoxycholic acid).

Any reference to a bile acid as used herein includes reference to a bile acid or a salt thereof. The term "bile acid" may also be used interchangeably with "bile acids", "bile salt", "bile salts" and "bile acid/salt". It is understood that the compositions comprise at least one bile acid, and could for instance comprise two or more bile acids. The at least one bile acid to be used could be chosen from primary bile acids and secondary bile acids and salts thereof. During physiological conditions, dietary fats are degraded in the upper gut lumen into fatty acids and monoglycerol that are then absorbed by the mucosa. After bariatric surgery, and during other conditions with low capacity for luminal lipid degradation, the concentration free fatty acids will be unphysiologically low in the upper gut.

It follows that the composition according to the invention comprises at least one fatty acid or a salt thereof, wherein said at least one fatty acid is saturated or unsaturated. The unsaturated fatty acids may have a cis or trans configuration. Said at least one fatty acid is for instance a short chain fatty acid (SCFA<6 carbons in aliphatic tail), eg butyrate, a medium chain fatty acid (MCFA, 6-12 carbon atoms in aliphatic tail, linear or branched), eg saturated caprylic acid (8 carbon atoms) and lauric acid (12 carbons), a long chain fatty acid (LCFA; 13-21 carbons), eg unsaturated palmitoleic acid, oleic acid, linoleic acid and saturated palmitic acid and stearic acid or a very long chain fatty acid (VLCFA, >21 carbon atoms). It is understood that the compositions comprise at least one fatty acid, and could for instance comprise two or more fatty acids. The at least one fatty acid or salt thereof used in the composition could be any one available and known to a skilled person within the art.

The composition as described herein comprises vitamin D. Vitamin D is a group of vitamins and includes cholecalciferol (vitamin D3), alfacalcidol, calcitriol. The composition described herein includes vitamin D which is present as vitamin D3, or at least mainly consists of vitamin D3. In another aspect of the invention calcium is present as a salt, as a $Ca^{2+}$-salt, for instance as a calcium citrate, calcium carbonate, or any calcium phosphate salt.

In an aspect of the invention a composition is provided wherein the amount of calcium and vitamin D in the composition is present as the recommended daily intake (RDI), less or more. The recommended daily intake of calcium is 1000 mg/day (milligrams/day) for an adult, and levels up to 1300-2500 mg/day is recommended for some people, for example elderly and youths, and the recommended daily intake of vitamin D is 600 IU/day corresponding to 15 (μg) for an adult and levels up to 800 IU/day (20; μg) is recommended for elderly people. The composition of the invention may comprise the recommended daily intake of vitamin D or comprise less or more, and up to 50,000 IU/day, corresponding to 1250 μg/day depending on the purpose of the composition, i.e. dependent on how many times a day the composition is to be given.

The amount of calcium may be present in the composition in the range of 100-2500 mg, eg in the range of 200-2000, eg in the range 300-1500 mg, eg in the range 400-1000 mg, eg 400-800 mg or 400-600 mg. The amount of calcium may be present in the composition in the amount of about 300, 400, 500, 600, 700, 800, 900, 1000, 1100, 1200, 1300, 1400, 1500, 1600, 1700, 1800, 1900, 2000, 2100, 2200, 2300, 2400, 2500 mg. The amount of vitamin D, for instance vitamin D3, may be present in an amount of 5-1250 μg, eg in the range of 10-1000, or 20-800, such as 100, 200, 300, 400, 500, 600, 700, 800 μg, and in the lower range of about 10, 11, 12, 13, 14, 15, 16, 17, 18, 19 or 20, 30, 40, 50, 60, 70, 80, 90 μg. The amount of vitamin D and calcium in the composition may be adjusted to provide optimum desired response (eg a therapeutic or prophylactic response).

The amount of said at least one bile acid in the composition is present in a range giving an intra-intestinal concentration of about $1 \times 10^{-7}$ to $1 \times 10^{-3}$ M, that corresponds to about 0.001 mg/kg to about 100 mg/kg, for instance 0.1 mg/kg to about 50 mg/kg, eg 2-40 mg/kg, eg 4-30 mg/kg, eg 6-20 mg/kg, eg 8-15 mg/kg, eg 4, 5, 6, 7, 8, 9, 10, 11, 12, 13, 14, 16, 17, 18 mg/kg, As for vitamin D and calcium the composition may be adjusted with reference to the said at least one bile acid to provide optimum desired response in a single dose or multiple doses.

The amount of said at least one fatty acid in the composition is present in a sufficient amount in the range of 0.5 g to about 20 g/day, eg 1-18, eg 3-15 g, eg 5-12 g, 7-10. The given ranges are in line with recommended intake of essential fatty acids. The composition may be adjusted with reference to the amount of fatty acid(s) to provide optimum desired response in a single dose or multiple doses. Several aspects have to be considered in the selection of the bile salts and fatty acids, e.g. solubility, possible toxicity and adverse side effects, palatability in peroral compositions, as well as their status as to whether they are considered food additives or pharmaceuticals. In an aspect of the invention a composition comprising a. at least one bile acid, or salt thereof, in an amount to provide an intra-intestinal concentration of about $1 \times 10^{-7}$ to $1 \times 10^{-3}$ M;
b. at least one fatty acid or a salt thereof, in an amount of 0.5 g to about 20 g;
c. calcium, in an amount of 100-2500 mg; and
d. vitamin D, in an amount of 800-2500 mg.

Example of the composition comprises:

a) at least one bile acid, or salt thereof, selected from the primary bile acids cholic acid (CA) and chenodeoxycholic acid (CDCA), and their corresponding conjugated forms glycocholic acid (GCA) and glycochenocholic acid (GCDCA), respectively, or their corresponding secondary bile acid deoxycholic acid (DCA), lithocholic acid (LCA), ursodeoxycholic acid (UDCA) and hyodeoxycholic acid (HDCA), and their corresponding conjugated forms are glychodeoxycholic acid (GDCA), glycolithocholic acid (GLCA), glycoursodeoxycholic acid (GUDCA), and, glycohyodeoxycholic acid (GHDCA), respectively in an amount to provide an intra-intestinal concentration of about $1 \times 10^{-7}$ to $1 \times 10^{-3}$ M;

b) at least one fatty acid selected from short chain fatty acid (SCFA<6 carbons in aliphatic tail), eg butyrate, a medium chain fatty acid (MCFA, 6-12 carbon atoms in aliphatic tail, linear or branched), eg saturated caprylic acid (8 carbon atoms) and lauric acid (12 carbons), a long chain fatty acid (LCFA; 13-21 carbons), eg unsaturated palmitoleic acid, oleic acid, linoleic acid and saturated palmitic acid and stearic acid or a very long chain fatty acid (VLCFA, >21 carbon atoms) or a salt thereof, in an amount of 0.5 g to about 20 g;

c) calcium, in an amount of 100-2500 mg; and d) vitamin D, such as vitamin D3, in an amount of 800-2500 mg.

This composition is intended for once daily administration. Suitable adjustments may be done for providing composition for administration twice, thrice, etc per day. The composition as defined above is for use as medicament.

In an aspect of the invention the composition is formulated for oral delivery. The composition is not limited to be formulated for oral delivery and could also be formulated for parenteral delivery, intravenous infusion or injection. When formulated for oral delivery, the composition may be delivered before intake of food, pre-prandial, and/or after intake of food, post-prandial. For example, the composition can be delivered before, during and/or after a meal.

In an aspect of the invention, the composition is in a liquid form or solid form. When the composition is formulated as a solid form it may be formulated as a chewing tablet, effervescent tablet, powder, pill, liquid, gel, tablet or capsule. In order to formulate the before mentioned solid forms other well-known carriers may be incorporated in such solid forms. Such carriers are well known to a skilled person and includes for instance solvents, dispersion media, coatings, flavours, antibacterial and antifungal agents, and isotonic agents and the like that are physiologically compatible. Examples of such carriers include one or more of water, saline, phosphate buffered saline, dextrose, glycerol, ethanol and the like as well as combinations thereof. Often it is preferable to use isotonic agents, for example sugars, polyalcohols such as mannitol, sorbitol or sodium chloride.

In an another aspect of the invention, there is provided a method for prevention and/or treatment of osteoporosis caused by calcium deficiency, mal absorption conditions caused by calcium deficiency or pathological bone conditions caused by calcium deficiency or bone mineral density loss caused by calcium deficiency or for treatment of osteoporosis by preventing bone mineral density (BMD) loss in Roux-en-Y gastric bypass (RYGB) individuals or sleeve gastrectomy (SG) individuals in a mammal, eg a human individual, by administering a composition comprising at least one bile acid or a salt thereof, and at least one fatty acid or salt thereof to an individual in need thereof. By administering a composition as indicated above expression of vitamin D-receptor co-activator Hsp90β is induced, for increasing vitamin D-induced calcium uptake.

In another aspect, the present invention is related, to a dietary or nutritional supplement comprising a composition comprising a bile acid or salt thereof and a fatty acid or a salt thereof and optionally calcium and vitamin D. Other conventional components for dietary or nutritional supplements may naturally also be added to such a supplement.

In an aspect of the invention the dietary supplement comprises other micronutrients such as iron, magnesium, zinc, copper, and vitamins, e. g. vitamin A, vitamin D, or vitamin E, and other conventional ingredients. Such conventional components are known to a skilled person within the art and examples are fillers, binders, humectants, disintegrating agents, buffering agents, excipients, adjuvants, antioxidants, preservatives.

In an aspect of the invention the composition comprises
a) at least one bile acid or salt thereof;
b) at least one fatty acid or a salt thereof;
c) calcium;
d) vitamin D; and optionally,
e) one more components selected from the group of micronutrients, e g components selected from the group consisting of iron, magnesium, zink, copper, and vitamins, eg vitamin A, vitamin D or vitamin E; and optionally,
f) one or more components selected from fillers, binders, humectants, disintegrating agents, buffering agents, excipients, adjuvants, antioxidants, preservatives.

In an embodiment of the invention the composition comprises
a) glycocholic acid (GCA), as the at least one bile acid or salt thereof;
b) oleic acid, or butyric acid, as the at least one fatty acid or a salt thereof;
c) calcium;
d) vitamin D; and optionally,
e) one more components selected from the group of micronutrients, e. g. components selected from the group consisting of iron, magnesium, zink, copper, and vitamins, e. g. vitamin A, vitamin D or vitamin E; and optionally,
f) one or more components selected from fillers, binders, humectants, disintegrating agents, buffering agents, excipients, adjuvants, antioxidants, preservatives.

Particularly, the at least one bile acid (a) is glycocholic acid (GCA), and, the at least one fatty acid (b) is butyric acid, together with components c) to f).

Particularly, the at least one bile acid (a) is glycocholic acid (GCA), and, the at least one fatty acid (b) is oleic acid, together with components c) to f).

The composition may be intended for use as dietary supplement. A dietary or nutritional supplement may contain in addition to the above described composition other vitamins and micronutrients that has a beneficial effect on the human health.

The above described aspects in relation to the composition of the invention, as also disclosed in the claims, is also applicable to the aspect of dietary and nutritional supplement.

One skilled in the art will appreciate further features and advantages of the invention based on the above-described embodiments. Accordingly, the invention is not to be limited by what has been particularly shown and described in the examples or figures.

According to another aspect of the invention, there is provided use of at least one bile acid or salt thereof, at least one fatty acid or a salt thereof, one or more vitamin D, and calcium, or salt thereof, in the manufacture of a medicament for the treatment and/or prevention of osteoporosis caused by calcium deficiency, inflammatory and malabsorption conditions causing calcium deficiency, bone disorders caused by calcium deficiency, or bone mineral density (BMD) loss caused by calcium deficiency, or for treatment of osteoporosis by preventing bone mineral density (BMD) loss in Roux-en-Y gastric bypass (RYGB) individuals or sleeve gastrectomy (SG) individuals, or individuals treated by other similar surgical techniques. Effects and features of the above aspect of the present invention are analogous to those described above. The compositions described herein are intended for use as medicament in treatment of the diseases and disorders disclosed above.

According to another aspect of the invention, there is provided compositions comprising at least one bile acid or salt thereof, and at least one fatty acid or a salt, wherein said at least one bile acid is one of the above mentioned bile acids and said at least one fatty acid is one of the above mentioned fatty acids.

EXPERIMENTAL

The objective of the experiments is to investigate ways to improve vitamin D-induced calcium uptake in the proximal small intestine for instance in patients that have undergone RYGB or SG surgery. The before said is tested by the addition of a specific bile acid (or human bile) and a fatty acid in order to induce expression of the vitamin D-receptor co-activator Hsp 90β. By inducing Hsp 90β, expression of the vitamin D induced calcium transport can be substantially increased, i.e. normalized in any kind of patient in need of increased calcium uptake, for instance in RYGB patients, and possibly also SG patients.

Caco-2 Cell Line

Caco-2 cell line is a continuous line of heterogeneous human epithelial colorectal adenocarcinoma cells developed by the Sloan-Kettering institute for Cancer Research. The cells are derived from the colon, or large intestine, with carcinoma but when these cells are cultured under specific conditions they become differentiated and polarized making their phenotype, morphologically and functionally resemble the enterocytes that line the small intestine.

Caco-2 cells are found to express tight junctions, microvilli, and a number of enzymes as well as transporters that normally are characteristics of such enterocytes: peptidases, esterases, P-glycoprotein, uptake transporters for amino acids, bile acids, carboxylic acids, etc. Microscopically Caco-2 cell cultures are heterogeneous and this theory is supported by the characteristics of the cells showing diverged significant results from different investigations around the world. Caco-2 cells are used commonly not as individual cells, but as a confluent monolayer on cell culture insert filter. This form of culturing lead to the cells differentiating to form a polarized epithelial cell monolayer that provides a physical and biochemical barrier to passage of ions and small molecules. Caco-2 monolayer culture is a widely used in vitro model of the human small intestinal mucosa to investigate the absorption of orally administered drugs.

Caco-2 Cell Culture

Caco-2 cells with a passage or about 45 (number of time they have been divided) (Sigma-Aldrich Stockholm Sweden) were cultured in Dulbecco's Modified Eagle's Medium (Life Technologies Invitrogen AB, Lidingo, Sweden), with 10% Foetal Bovine Serum (FBS) (Life Technologies), 1% Non Essential Amino Acid (NEAA) (Life Technologies), 100 IU/mL Penicillin Streptomycin (Pen-Strep) (Life Technologies). The cells were incubated in 37° C. with 5% $CO_2$ and cultured in a cell culture flask (BD Falcon®, VWR Internationals, Stockholm, Sweden) and the medium was changed at Monday, Wednesday and Friday every week.

The cells were cultured for approximately 1 week before they were detached (0.25% trypsin-EDTA, Life Technologies) and seeded in 6 well plates with semipermeable filter inserts (3 μm pore size, BD Biosciences, Le Pont de Claix, France), 200 000 cells/well. At confluence the culture medium was changed to FBS-free in both the upper and lower well compartment and to the lower compartment also a mixture of 10 μL/mL insulin, 0.55 μg/mL transferring and 6.7 ng/mL selenium (ITS, Life Technologies) was added to establish cell polarity and structural differentiation (6-7). The cell monolayers were let to cultivate for 14 days before experiments.

The cells were then stimulated for 24 h or 48 h with 10 mM with fatty acid and human bile or biliary acids, or a combination of both, in the upper "luminal" compartments (treated cells) and the other were left as control (untreated cells). Bile acids are present as components of bile.

Western Blot Analysis

For the protein harvesting, the cells was scraped into lysis buffer in protein kinase blocking solution (1% Triton x-100, EDTA; ethylenediaminetetraacetic acid) containing protein kinase inhibitor buffer (10 mM potassium phosphate buffer pH 6.8, 10 mM 3-[(3-cholamidopropyl) dimethylammonio]-1-propane sulphonate (CHAPS: Boehringer Mannheim, Mannheim, Germany) and protease inhibitor cocktail tablet Complete (Roche Diagnostics AB, Stockholm, Sweden). After shaking several times on ice, the cell debris was removed by centrifugation (10000×g for 10 min at 4° C.) and the supernatant's protein content was analysed using the Bradford method.

Samples were diluted in SDS buffer and heated at 70° C. for 10 min before they were loaded on a NuPage 10% Bis-Tris gel, and electrophoresis run using a MOPS buffer (Invitrogen AB, Lidingo, Sweden). One lane of each gel was loaded with prestained molecular weight standards (See-Blue, NOVEX, San Diego, Calif., USA). After the electrophoresis the proteins were transferred to a polyvinyldifluoride membrane (Amersham, Buckinghamshire, UK), which was incubated with Hsp 90β antibody (abcam; ab80159, Cambridge, UK), and a secondary alkaline phosphatase conjugated goat anti-rabbit IgG antibody (Santa Cruz) and CDP-Star (Tropix, Bedford, Mass., USA) were used as a substrate to identify immunoreactive proteins by means of chemiluminescense. Images were captured by a Chemidox XRS cooled CCD camera, and analyzed with Quantity One software (BioRad laboratories, Hercules, Calif., USA).

$Ca^{2+}$ Uptake and Transport

The Caco-2 cells were cultivated in on permeable support for 11-14 days, slightly modified according to Giuliano A. R., & Wood R. J. On the day of the experiments the trans-epithelial electrical resistance was measured and only preparations with values between 400 and 900 Ohms×cm$^2$ were counted. Tested substances were given in the top compartment and effect as read after 24 to 48 h. $Ca^{2+}$ flux was measured using liquid scintillation comparing the lower compartment with the upper.

Experiment 1

In this experiment the Caco-2 cells were tested with the fatty acid butyric acid (alternatively called: butyrate), the bile acid glycocholic acid (GCA), or a combination of butyric acid and GCA.

The cells were grown to confluence and then incubated with vehicle, butyric acid, bile acid, or a combination of bile acid and butyric acid, for 48 h. Cells were then harvested and total cellular proteins were extracted and analysed using western blotting. Hsp 90β expression is presented normalized to the expression of the non-regulated control protein GAPDH. The effect of the conjugated bile acid GCA, with and without the addition of the fatty acid butyric acid, on Hsp 90β expression in cultured Caco-2 cells is presented in FIG. 1.

The results show that GCA had no effect by itself on Hsp 90β, but only in conjunction with butyric acid there was a prominent and highly significant increase of Hsp 90β protein expression compared to the vehicle treated control cells.

Experiment 2

Figure 2:
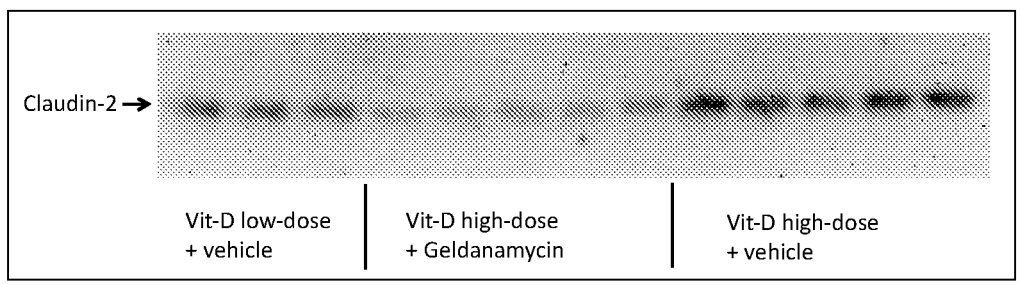
FIG. 2 discloses a western blot, and that vitamin-D has an effect to increase claudin-2 protein expression in cultured Caco-2 cells in a dose-dependent fashion, thereby facilitating "passive" calcium absorption. Suppression of the vitamin-D coactivator Hsp 90β by the specific inhibitor geldanamycin, also suppresses claudin-2 expression, obviously via inhibition of vitamin-D activity, thereby demonstrating that Hsp 90β is important also for "passive" calcium absorption.

Claudin-2 is a permissive tight-junction protein that increases calcium absorption in the distal small intestine by the paracellular route, usually referred to as "passive" calcium absorption. FIG. 2 shows that vitamin-D has an effect to increase claudin-2 protein expression in Caco-2 cells in a dose-dependent fashion, thereby facilitating "passive" calcium absorption. Suppression of the vitamin-D coactivator Hsp 90β by the specific inhibitor geldanamycin, also suppresses claudin-2 expression, obviously via inhibition of vitamin-D activity, thereby demonstrating that Hsp 90β is important also for "passive" calcium absorption. Therefore, facilitation of Hsp 90β expression in the small intestine should have beneficial effect also on passive calcium absorption in the human small intestine. The Caco-2 cells were cultured under the same experimental conditions as in experiments 1. Vitamin D was added at concentrations of 10 μM (low-dose) or 100 μM (high-dose). Geldanamycin was added at a concentration of 0.5 μM.

Experiment 3

Figure 3:
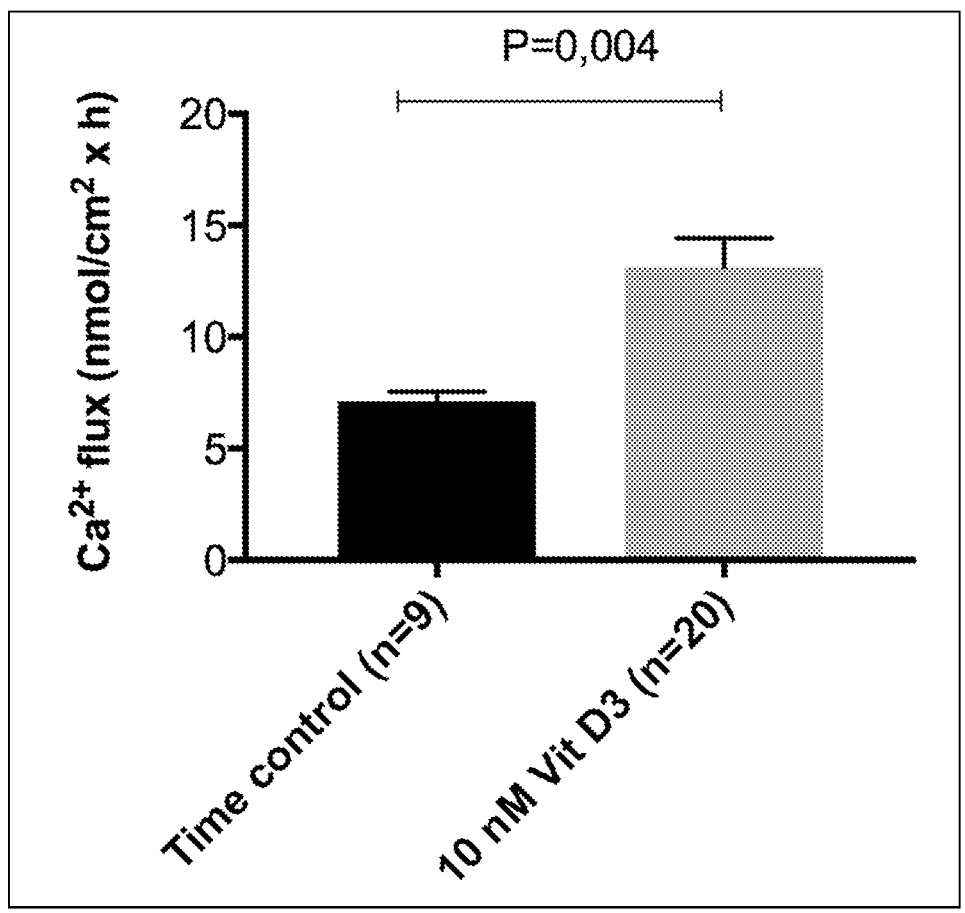
FIG. 3 discloses the effect of presence of vitamin D3 on the calcium uptake.

In the present experiment the Caco-2 cells were cultured and grown to epithelium-shaped confluence over 14 days. The following experiments were performed according to Giuliano A. R., & Wood R. J. The effect of 10 nM 1.25 $(OH)_2$-vitamin D3 on the calcium transport was tested during the last 48 hours. Flux was tested without calcium ($Ca^{2+}$) gradient, concentration of calcium was 1.8 mM on each side of the layer of cells. Thus active transport of vitamin D was confirmed. The result is presented in FIG. 3.

Experiment 4

In the present experiment the Caco-2 cells were cultured and grown to epithelium-shaped confluence over 12 days. The cells were then grown in another 4 days in presence of 0.1 mM GCA, or in presence with 0.5 mM butyrate, or in presence of the GCA and butyrate in combination.

Figure 4:
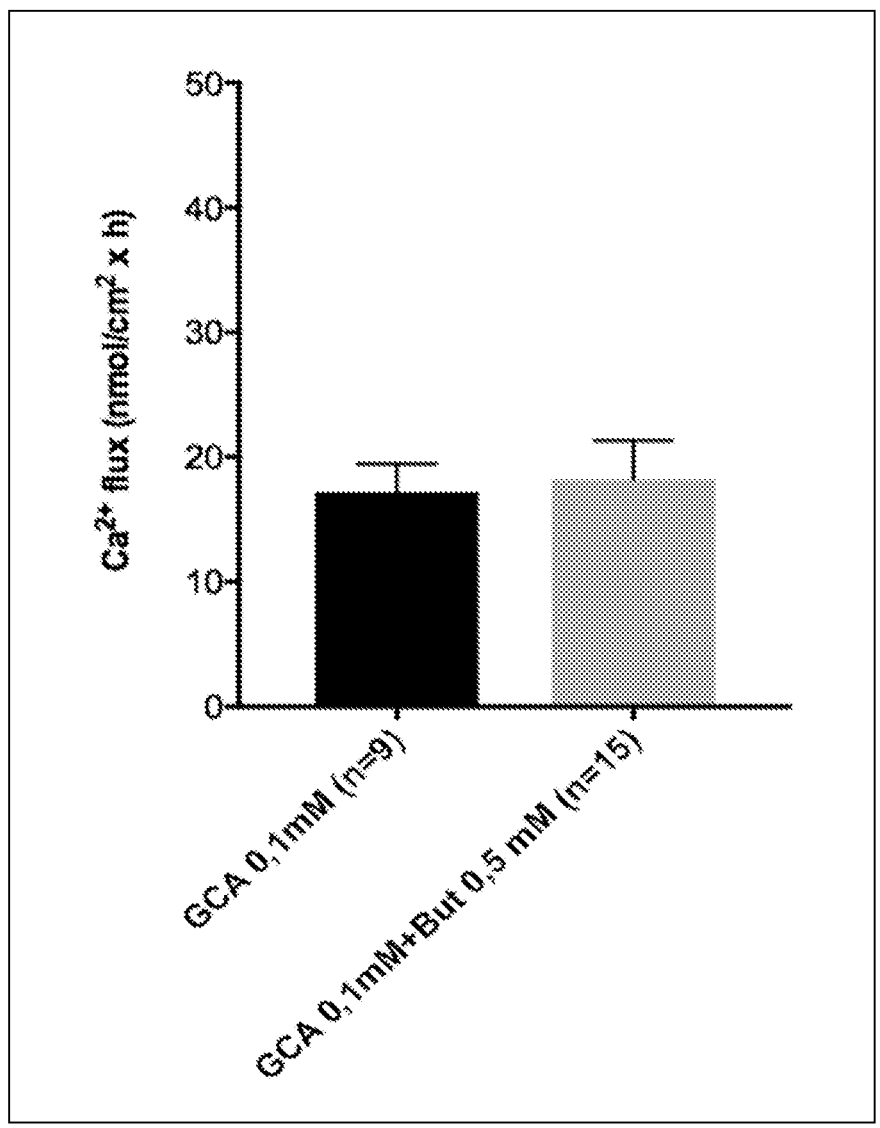
FIG. 4 discloses the effect of bile acid, fatty acid, vitamin D3 on calcium uptake (without gradient).

The effect of 10 nM 1.25$(OH)_2$-vitamin D3 on the calcium transport was tested during the last 48 hours. Flux were tested without a calcium ($Ca^{2+}$) gradient, the concentration of calcium was 1.8 mM on each side of the layer of cells. The result is presented in FIG. 4 (wherein means±SEM are indicated).

The experiment shows active transport through the Caco-2 epithelium layer. It can be concluded the rate of transport is in the same order of magnitude as with 1.25 $(OH)_2$-vitamin D3 alone, and that there is no additional effect of combining a bile acid together with a fatty acid in the absence of a calcium gradient.

Experiment 5

In the present experiment the Caco-2 cells were cultured and grown to epithelium-shaped confluence over 12 days. The cells were then grown in another 4 days in presence of Vitamin D3 alone, or in combination with 0.5 mM butyrate, or in combination with 0.1 mM GCA, or in combination with both GCA and butyrate, or 0.1 mM TCA, or in combination with both TCA and butyrate.

The effect of 10 nM 1.25(OH)$_2$-vitamin D3 on the calcium transport was tested during the last 48 hours. Flux was tested with a calcium (Ca$^{2+}$) gradient, with 40 mM on the apical side and 1.8 mM on the basolateral side.

Figure 5:
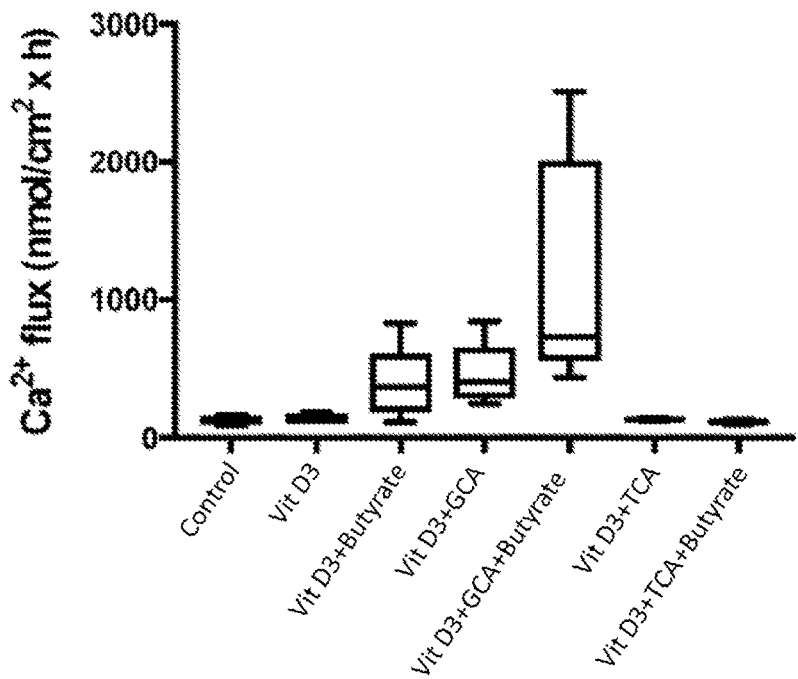
FIG. 5 discloses the effect of bile acid, fatty acid, vitamin D3 on calcium uptake (with gradient).

The effect was measured with Kruskall-Wallis test, contrasted with Dunn's multiple comparison test. The result is presented in FIG. 5 (wherein means±95%-confcence-intervals are indicated). Herein, it can be concluded that an increased uptake of calcium is achieved with the combination of vitamin D, GCA and butyrate. However, it can also be concluded that no uptake was achieved with vitamin D, TCA and butyrate.

Experiment 6

In the present experiment the Caco-2 cells were cultured and grown to epithelium-shaped confluence over 12 days. The cells were then grown in another 4 days in presence of Vit D3 alone, or in combination with 0.5 mM butyrate, or in combination with 0.1 mM GCA, or in combination with both GCA and butyrate, or in combination with GCA and oleic acid.

The effect of 10 nM 1.25(OH)$_2$-vitamin D3 on the calcium transport was tested during the last 48 hours. Flux was tested with a calcium (Ca$^{2+}$) gradient, with 40 mM on the apical side and 1.8 mM on the basolateral side.

Figure 6:
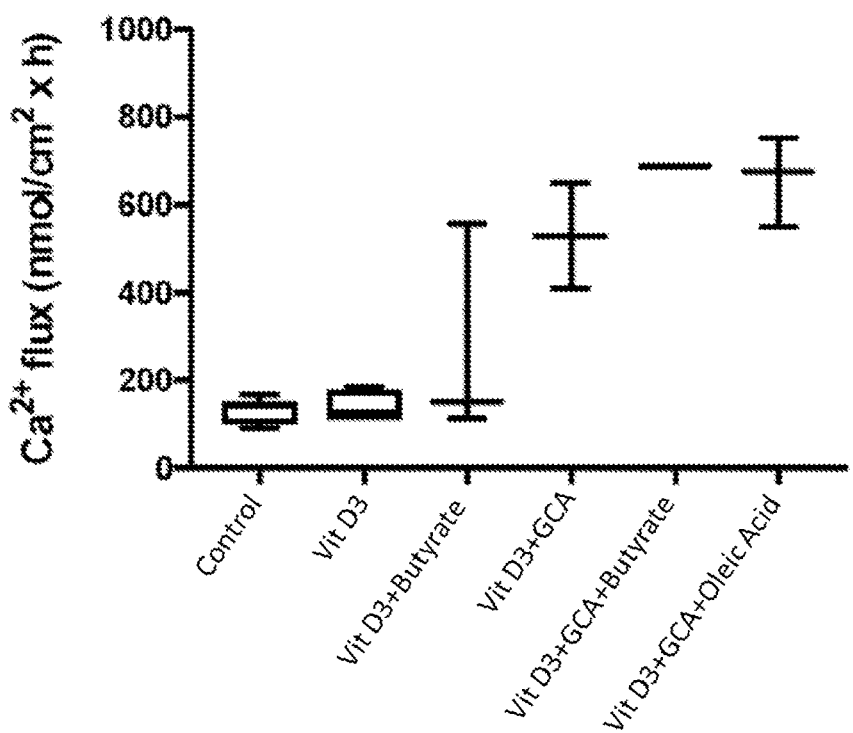
FIG. 6 discloses the effect of bile acid, fatty acid, vitamin D3 on calcium uptake.

The effect was measured with Kruskall-Wallis test, contrasted with Dunn's multiple comparison test. The result is presented in FIG. 6 (means±95%-confidence-intervals). Herein, it can be concluded that an increased uptake of calcium is achieved with the combination of vitamin D, GCA and butyrate, increased uptake was also achieved with vitamin D, GCA and oleic acid.

REFERENCES

Elias et al., Bone Mineral Density and expression of vitamin D receptor-dependent calcium uptake mechanisms in the proximal small intestine after bariatric surgery, Br J Surg. 2014 November; 101(12):1566-75).
Crawford et al. 'Increased bone turnover in type 2 diabetes patients randomized to bariatric surgery vs. medical therapy at 5 years', Endocrine practice, 2018, DOI: 10.4158/EP-2017-0072).
Hewit S et al., Secondary hyperparathyroidism, vitamin D sufficiency and serum calcium 5 years after gastric bypass and duodenal switch, Obes Surg. 2013, March; 23(3):384-90).
Schafer A L, et al., Intestinal Calcium Absorption Decreases Dramatically After Gastric Bypass Surgery Despite Optimization of Vitamin D Status. J Bone Miner Res. 2015, August; 30(8):1377-85).
Giuliano A. R., & Wood R. J. ('Vitamin D-regulated calcium transport in Caco-2 cells: unique in vitro model', Am. J. Physiol. 260 (Gastrointest. Liver Physiol. 23): G207-G212, 1991).
Goldenberg D et al., Thyroidectomy in patients who have undergone gastric bypass surgery. Head Neck. 2018 June; 40(6):1237-1244.

The invention claimed is:

1. A method for treating a calcium absorption deficiency in a patient comprising administering to said patient an amount of a composition comprising
   glycocholic acid (GCA), or a salt thereof, and
   butyric acid, or a salt thereof.
2. A method for treating osteoporosis, calcium malabsorption conditions or bone disorders in a patient comprising administering to said patient an amount of a composition comprising
   glycocholic acid (GCA), or a salt thereof, and
   butyric acid, or a salt thereof.
3. A method for reducing bone mineral density (BMD) loss in a patient comprising administering to said patient an amount of a composition comprising
   glycocholic acid (GCA), or a salt thereof, and
   butyric acid, or a salt thereof.
4. The method of claim 1, wherein the patient is a Roux-en-Y gastric bypass (RYGB) patient or a sleeve gastrectomy (SG) patient.
5. The method of claim 1, wherein the composition further comprises vitamin D, and wherein the vitamin D in the composition is present in an amount equal to the recommended daily intake (RDI) or less.
6. The method of claim 1, wherein the composition further comprises calcium, and wherein the calcium in the composition is present in an amount equal to the recommended daily intake (RDI) or less.
7. The method according to claim 5, wherein the vitamin D comprises vitamin D3.
8. The method according to claim 6, wherein the calcium is calcium carbonate, calcium citrate, calcium phosphate or mixtures thereof.
9. The method according to claim 1, wherein the composition further comprises at least one of a vehicle, excipient, lubricant, flavour, sweetener, binder, or disintegrant.
10. The method according to claim 1, wherein the composition is formulated for oral delivery, parenteral delivery, intravenous infusion, or injection.
11. The method according to claim 1, wherein the composition is in solid form.
12. The method according to claim 1, wherein the composition is formulated as a powder, pill, tablet, or capsule.
13. The method according to claim 1, wherein the composition is a nutritional or dietary supplement.
14. The method of claim 1, wherein the composition further comprises oleic acid, or a salt thereof.
15. The method of claim 2, wherein the composition further comprises oleic acid, or a salt thereof.
16. The method of claim 3, wherein the composition further comprises oleic acid, or a salt thereof.

* * * * *